United States Patent [19]

Patterson

[11] 4,097,239
[45] Jun. 27, 1978

[54] TWO-FLAME BURNER FOR FLAME PHOTOMETRIC DETECTION

[75] Inventor: Paul L. Patterson, Walnut Creek, Calif.

[73] Assignee: Varian Associates, Inc., Palo Alto, Calif.

[21] Appl. No.: 772,710

[22] Filed: Feb. 28, 1977

[51] Int. Cl.² .................. G01J 3/48; G01N 31/12
[52] U.S. Cl. .................. 23/232 R; 23/254 R; 23/253 PC; 23/230 PC; 356/87; 356/187; 431/4; 431/126; 431/284
[58] Field of Search ............ 23/232 R, 254 R, 255 R, 23/253 PC, 230 PC; 356/87, 187; 431/4, 126, 284, 285

[56] References Cited

U.S. PATENT DOCUMENTS

| 2,562,874 | 7/1951 | Weichselbaum | 431/126 X |
|---|---|---|---|
| 2,603,085 | 7/1952 | Cannon, Jr. | 23/232 R X |
| 2,769,366 | 11/1956 | Honma | 356/87 |
| 3,208,333 | 9/1965 | Gilbert, Jr. | 431/4 |
| 3,695,812 | 10/1972 | Herron et al. | 356/87 X |
| 3,695,813 | 10/1972 | Griffith et al. | 356/87 X |

OTHER PUBLICATIONS

Krost et al., Anal. Chem., 45, 1800 (1973).

*Primary Examiner*—Robert M. Reese
*Attorney, Agent, or Firm*—John J. Morrissey; Stanley Z. Cole; Gerald M. Fisher

[57] ABSTRACT

A two-flame burner is used in a flame photometric detector for analyzing a sample material. The sample material is introduced via a first conduit structure into a hydrogen-rich first flame, and the combustion products and excess hydrogen from the first flame are passed via a second conduit structure into an oxygen-containing environment. A second flame is maintained at the exit end of the second conduit structure. The first and second conduit structures are composed of material that does not contribute to the coloration of the second flame during operation of the detector. Particular constituents of the sample material are detected by observing the presence of colors in the second flame indicative of the constituents. For example, the presence of sulfur is indicated by a blue coloration, and the presence of phosphorus is indicated by a green coloration. The presence of nitrogen is indicated by a coloration of the second flame resulting from a chemiluminescent molecular recombination of nitric oxide and oxygen atoms to form nitrogen dioxide molecules. The presence of any hydrocarbon can be indicated by a flame coloration resulting from a chemical reaction indicative of elemental carbon.

29 Claims, 3 Drawing Figures

TWO-FLAME BURNER FOR FLAME PHOTOMETRIC DETECTION

BACKGROUND OF THE INVENTION

This invention is a further development in the field of flame photometric detection, and pertains to a two-flame burner for use in the flame photometric detection of chemical substances. A particular application for this invention is in the detection of compounds in the effluent from a gas chromatograph.

As is well known in the art of flame photometry, a typical flame photometric detector comprises a burner structure for producing a flame, a flame viewing window, an optical filter for spectral selection of light from the flame, and a photomultiplier tube. The detection of chemical compounds by the flame photometric technique has been found to depend upon the chemical reaction of such compounds with H, OH and O radicals in a flame produced by the burning of a mixture of hydrogen and oxygen, or a mixture of hydrogen and air. The primary $H_2$ and $O_2$ fuel gases react in the flame to yield the combustion product $H_2O$ and the radicals H, OH and O. The various chemical reactions occurring in an $H_2/O_2$ flame include:

(1) $H_2 + O_2 = H_2O + O$
(2) $H_2 + O_2 = OH + OH$
(3) $3H_2 + O_2 = 2H_2 + 2H$
(4) $H_2 + OH = H_2O + H$
(5) $H_2 + O = OH + H$
(6) $OH + O = O_2 + H$

The concentration of these H, OH, and O radicals in the flame is believed to be primarily responsible for the chemical decomposition of organic molecules that might be introduced into the flame, and for the processes that result in the appearance of colorations in the flame that are characteristic of the constituents of such molecules.

The physical and chemical environment of a flame can be characterized as a gaseous volume containing spatial variations in both gas temperature and chemical species. Consequently, a flame quite commonly exhibits more than one region of coloration. When a flame is used in flame photometric detection, the light produced by the decomposition of a given chemical species may often be masked by interfering light from other chemical species. The magnitude of such interfering light is dependent upon the kinds of gases being mixed together in the flame, the flow rates of those gases, the geometry and dimensions of the flame burner, and the materials of construction of the flame burner.

When a flame photometric detector is used in conjunction with a gas chromatographic column, consideration must also be given to the fact that compounds in the effluent from the gas chromatograph are frequently molecules of highly complex structure. Upon entering the flame environment, such molecules can so perturb the temperature and species gradients in the flame as to adversely affect the production of light of the desired coloration.

Most applications of flame photometric detectors with gas chromatographs have hitherto been directed to the selective detection of only sulfur-bearing or phosphorus-bearing compounds. If a sulfur-bearing molecule is introduced into a hydrogen-rich $H_2/O_2$ or air flame, a blue emission appears in the flame. This characteristic blue emission is attributable to excitation of the $S_2$ molecule. Although the chemical mechanisms for the formation of the $S_2$ molecule are not absolutely confirmed, kinetic data suggest that sulfur-bearing compounds upon encountering H, OH and/or O radicals in the flame are decomposed to yield $H_2S$ as a primary combustion product. The $H_2S$ is then converted to $S_2$ in a series of reactions such as:

(7) $H_2S + H \rightarrow SH + H_2$
(8) $SH + H \rightarrow S + H_2$
(9) $SH + S \rightarrow S_2 + H$ The S molecule is thereupon excited and subsequently relaxes to yield the characteristic blue sulfur emission in a reaction such as:

(10) $H + H + S_2 = S_2^* + H_2$

The H radical is necessary in the formation of the blue sulfur emission.

If a phosphorus-bearing molecule is introduced into a hydrogen-rich $H_2/O_2$ or air flame, a green emission is noted. This characteristic green emission is attributable to the HPO molecule. Although the chemical mechanisms for the formation of the HPO molecule are not absolutely confirmed, kinetic data suggest that phosphorus-bearing compounds, upon encountering H, OH and O radicals in the flame, are decomposed to yield the PO radical as a primary combustion product. Two different mechanisms that have been suggested for the formation of the excited HPO molecule are:

(11) $H + PO + M = HPO^* + M$, where M represents some other species, and
(12) $OH + PO + H_2 = HPO^* + H_2O$ The H and OH radicals are necessary in the formation of the green phosphorus emission.

The burners described in U.S. Pat. Nos. 3,489,498 and 3,213,747 are representative of two different prior art techniques for the flame photometric detection of sulfur-bearing and phosphorus-bearing constituents in the effluent of a chromatographic column. In one of these prior art burners, a single hydrogen-rich flame is used both to decompose compounds in the gas chromatographic column effluent and to produce the desired blue or green coloration indicative of the presence of sulfur or phosphorus, respectively. The optimized gas flow rates and geometry of the burner are such that interfering light from hydrocarbons occurs at the base of the flame in close proximity to the burner orifices, whereas the sulfur and phosphorus emissions occur in the diffuse upper portions of the flame. These upper portions of the flame are observed by photomultiplier means. Selectivity is enhanced by the use of an opaque shield disposed about the flame base so as to prevent hydrocarbon emissions from reaching the field of view of the photomultiplier tube. Known limitations of this type of burner are related to its use of a single flame, and to perturbations of the environment of that flame caused by complex molecular structures present in the gas chromatographic effluent. Such flame perturbations can cause variations in sample response depending upon the structure of the sample molecule. Such flame perturbations can also cause quenching of the sample response in the simultaneous presence of a hydrocarbon background.

Also, complete extinction of the flame can occur in the presence of large quantities of a hydrocarbon compound, such as frequently occurs with solvents commonly used in gas chromatography. Such a hydrocarbon compound serves to starve the flame of oxygen, causing extinction thereof. Furthermore, because this type of burner uses a hydrogen-rich flame, large excesses of unburned $H_2$ are present in the exhaust gases and constitute a potential safety hazard.

It is instructive to consider the other type of prior art burner in some detail, in order to point out the limitations of the prior art. This other type of burner, known as the van der Smissen burner, is illustrated in FIG. 1. The van der Smissen burner is a special usage of the Smithells type flame separation technique, (A. Smithells and H. Inge, Trans. Chem. Soc., Vol. 61, p. 204, 1892) for spatially separating different reaction regions of a flame burning in ambient air by means of an optically transparent flame separation tube.

As shown in FIG. 1, a mixture of air and the effluent from a chromatographic column is introduced via a conduit 31 into the interior of a smooth bore tube 40. The tube 40 is optically transparent in the visual region of the electromagnetic spectrum and is fabricated from material such as quartz or Pyrex glass. Hydrogen gas is introduced into the interior of the tube 40 via a conduit 34. In operation, a hydrogen-rich first flame is ignited at the tip of the conduit 31 within the tube 40. Burned gases from this first flame are confined within the tube 40, and exit to ambient air at the upper tip of the tube 40, where excess $H_2$ that was unconsumed in the first flame burns in a second flame at the upper tip of the column 40. To initiate operation, the second flame is ignited first. Because of the upstream mix of $H_2$ and air in the column 40, and because of the smooth bore of the tube 40, the upper flame (i.e., the second flame) causes a flashback that ignites the lower flame (i.e., the first flame). Because both the lower and upper flames produce high temperatures, a water jacket 55 is used to cool the column 40 in the region between the flames in order to prevent excess heating of the quartz or Pyrex glass walls.

In the specification of the van der Smissen U.S. Pat. No. (3,213,747), the lower flame is described as having a bluish-white coloration, and the upper flame is described as having a bluish, reddish, or yellowish color in the absence of sulphur or phosphorus. Since it is well known that a pure $H_2/O_2$ or air flame normally emits no visible radiation, the colorations of the upper and lower flames are probably due to impurities outgassing from the hot quartz or Pyrex flame tips. For example, sodium is a common impurity in quartz and Pyrex glass, and Na outgassing from the hot tube 40 is likely to cause a yellow or orange flame coloration.

Where sulphur-bearing or phosphorus-bearing compounds are present in the column effluent, diffuse bands of blue and/or green occur in the zone 43 within the tube 40 between the lower and the upper flames. The blue band is indicative of the presence of sulphur-bearing constituents, and the green band is indicative of the presence of phosphorus-bearing constituents. Under optimized flow conditions, the green band occurs in a region that is spatially closer to the lower flame than the region in which the blue band occurs. In the van der Smissen technique, the presence of such blue and/or green bands is observed by optical viewing means through the transparent walls of the water jacket 55 and the tube 40. As discussed above, the blue emission is attributable to excitation of $S_2$ molecules produced by various chemical reactions occuring in the lower flame, and the green band is attributable to excitation of HPO molecules also produced by chemical reactions occurring in the lower flame. These $S_2$ and HPO molecules, of course, are again excited as they enter the upper flame upon exiting from the tube 40.

Where sulphur-bearing and/or phosphorus-bearing constituents are present in the column effluent, characteristic blue and/or green emissions are present in the core of the upper flame. However, according to the van der Smissen technique, the presence of such characteristic blue and/or green emissions is detected in the usual case by optical viewing of the expansion region in the tube 40 between the lower and the upper flames. Since the upper flame of the prior art van der Smissen burner is surrounded by a peripheral region that is colored white, yellow, blue or red, depending upon the type of material from which the column 40 is fabricated, this region of coloration masks the characteristic blue and/or green emissions that may be present in the core of the upper flame. Consequently, the upper flame cannot be used to detect low-level concentrations of sulfur and phosphorus.

An advantage of the van der Smissen burner is that the excess $H_2$ from the lower flame is burned in the second flame. Also, since there is always abundant $O_2$ at the second flame, the second flame will not be extinguished by large solvent peaks. The first flame probably is extinguished from time to time by large solvent peaks, but such extinguishing of the first flame presents no problem because flashback from the second flame automatically relights the first flame whenever the solvent concentration extinguishes the first flame. A disadvantage of the van der Smissen burner, however, is that a relatively cumbersome water cooling system must be used. Optical viewing of the region between the two flames must be accomplished not only through the wall of the tubing between the two flames, but also through the wall of the water jacket and through the water itself, which results in decreased sensitivity because of reflection, refraction and absorption effects.

Another disadvantage of the van der Smissen technique lies in the fact that the green and blue bands of coloration due to phosphorus and sulfur, respectively, appear at different spatial locations within the glow region 43. Hence, a change in detection mode from selective phosphorus detection to selective sulfur detection necessitates a spatial relocation of the optical axis of the viewing spectrophotometric device, (e.g., optical filter and photomultiplier tube). In addition, the exact spatial locations of the green and blue bands within the glow region 43 are highly dependent upon the magnitude of the flow rates of the gases entering through the conduits 31 and 34. Changes in these flow rates can require further relocation of the optical viewing axis in order to maintain optimum sample response.

With respect to the detection of nitrogen compounds by flame photometric detection techniques, the prior art methods have all been limited by poor detectability, poor linearity, or serious interferences from other compounds. Prior analytical methods have utilized all the major molecular band spectra of nitrogen compounds — namely, CN, NO, NH and $NH_2$. Flame emission spectra and analytical studies of nitrogen have been reviewed by R. Mavrodineaunu, *Analytic Flame Spectroscopy*, MacMillan and Co. (1970), pages 228-238.

Mavrodineanu describes the "nitrogen afterglow" sometimes seen in analytical flames as being due to continuum radiation from the reation $NO + O \rightarrow NO_2 + h\nu$. However, this radiation has not heretofore been utilized in any analytical method for determining the presence and quantity of N-compounds. This is probably because broad, featureless continuum radiation is generally less intense and is subject to more spectral interferences than are distinct molecular emission bands such as those mentioned above.

The detection of nitrogen compounds using a flame chemiluminescent method based upon the reactions $H + NO \rightarrow HNO^*$ and $HNO^* \rightarrow HNO + h\nu$ has been described by K. J. Krost, J. A. Hodgeson and R. K. Stevens, *Analytical Chemistry*, 45, 1800 (1973). Radiation from the reaction $HNO^* \rightarrow HNO + h\nu$ occurs in the spectral range of 650–760 nanometers, and is obtained in a hydrogen-rich oxy-hydrogen flame. However, in this reaction $SO_2$ constitutes a major source of interfering radiation. The detector described by Krost, et al. was shown to have a linear response for nitrogen oxides from 0.15 ppm to 60 ppm. For this detection mechanism to work effectively for a general class of organic nitrogen compounds, the organic N must be oxidized to NO or $NO_2$ in the flame, which is difficult to ensure in a flame that is hydrogen-rich.

SUMMARY OF THE INVENTION

It is an object of this invention to provide a dual-flame burner for analyzing chemical substances by the flame photometric detection technique.

More particularly, it is an object of this invention to provide a flame photometric detector in which complex chemical compounds, e.g., complex compounds in the effluent of a gas chromatographic column, or contaminants in the atmosphere, are initially combusted in a hydrogen-rich first flame so as to be reduced to combustion products consisting of molecules of much simpler chemical structure, and in which the combustion products and excess hydrogen from this first flame are subsequently combusted in a second flame that is spatially separated from the first flame. The purpose of the second flame is to provide a flame environment of radical chemical species, so as to generate characteristic optical emissions in the second flame that can be detected by conventional spectrophotometric means. Decomposition of the complex chemical compounds in the first flame serves to minimize perturbations in the temperature and species gradients of the second flame that might otherwise occur if the complex molecules were to enter the second flame.

It is a particular object of this invention to provide a flame photometric detector that is capable of reliably indicating and measuring the presence of sulfur-containing and phosphorus-containing constituents in sample materials, e.g., for indicating and measuring the extent of hydrogen sulfide in air for pollution control applications.

It is also a particular object of this invention to provide a technique for reliably indicating and measuring the presence of nitrogen-containing constituents in sample materials. According to this nitrogen detection technique, nitrogen-containing compounds are combusted in an oxygen-containing first flame to yield, among other combustion products, nitric oxide. The nitric oxide is then passed to a second flame, which is oxygen-rich, wherein the nitric oxide reacts with atomic oxygen to form nitrogen dioxide. This process of formation of nitrogen dioxide releases energy in the form of characteristic light emission in the second flame. This light is detectable by spectrophotometric means. The technique of this invention provides an enhancement of the NO + O reaction over that obtainable with prior art techniques, thereby permitting detection of the chemiluminescent molecular recombination of NO and O to form $NO_2$. In the prior art, this chemiluminescent molecular recombination was not detectable with sufficient precision for analytical purposes because of the predominance of interfering radiations from other reactions. The enhancement of the NO + O reaction in the present invention is the result of using the combustion products of the first flame as fuel for the second flame. This technique provides maximum mixing for the NO molecules in the fuel for the second flame, thereby assuring a diffuse volume rich in O atoms in which the NO + O reaction can take place.

It is further the object of this invention to provide a dual-flame burner constructed of materials of high thermal conductivity and low impurity content, such that hot burner components contribute only minimal interfering flame coloration to the second flame.

In the present invention, a means can be provided for maintaining the upper flame in an environment in which the oxygen content can be controlled, rather than in ambient air. Also, in the present invention, in contradistinction to dual-flame burners of the prior art, the combustion products and unburned gases from the lower first flame are carried within a non-transparent tube of high thermal conductivity, e.g., a stainless steel or alumina ceramic tube, to a region in which they are burned by an upper second flame. Detection of emissions that are characteristic of compounds in the sample being analyzed is accomplished by spectrophotometric viewing of the second flame. Unlike dual-flame burners of the prior art, the second flame of the present invention is not masked by a peripheral region of optical noise, because the excitation of materials outgassed from the structural members of the burner of this invention is substantially eliminated.

DESCRIPTION OF THE PREFERRED EMBODIMENT

Figure 1:
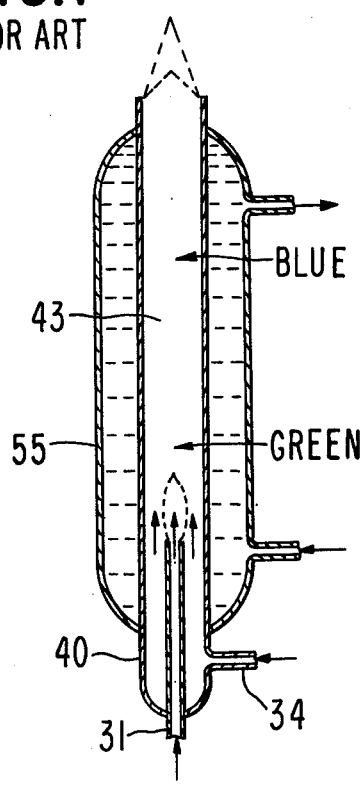
FIG. 1 is a schematic sectional view of a prior art flame photometric detection burner.
Figure 2:
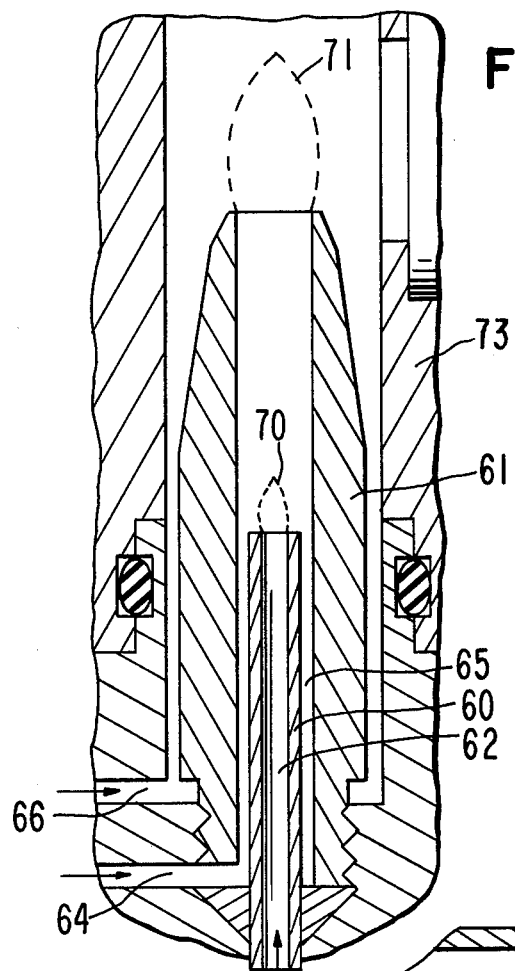
FIG. 2 is a cross sectional view, partially schematic, of a two-flame photometric detection burner according to the present invention.

A dual-flame photometric detection burner according to the present invention is illustrated in FIG. 2. Inner and outer flame tip members 60 and 61, respectively, are fabricated of a stainless steel, such as stainless-316, which has an extremely high thermal conductivity in comparison with fused quartz or Pyrex glass. For example, the thermal conductivity of stainless-316 in the range from 0° to 100° C is 0.037, and at 650° C is 0.050. The thermal conductivity of fused quartz on the other hand is 0.0033 at room temperature. Similarly, the thermal conductivity of most glasses is in the range from 0.0016 to 0.0029 at room temperature, with the thermal conductivity values rising 20% to 25% at 200° C. Alumina ceramic, which has a thermal conductivity close to that of stainless steel, could also be used for the flame tip members 60 and 61.

The inner flame tip member 60 is generally cylindrical structure having a central bore 62, which receives the sample to be analyzed, which may be the effluent from a chromatographic column. The upper end portion of the flame tip member 60 is of tubular configuration, e.g., of 0.12-inch outside diameter and 0.06-inch inside diameter, which fits within the surrounding outer flame tip member 61, also of tubular configuration, such that an annular clearance of approximately 0.01 inch exists between the outer wall of flame tip member 60 and the inner wall of the flame tip member 61. This annular clearance defines a gas-flow passageway 65. One or more conduits 64 permit entry of a gas flow into the annular volume 65.

In the preferred mode of operation, a mixture of an oxygen-containing gas and the gas to be analyzed (e.g., the effluent from a chromatographic column or a sample of ambient air to be analyzed for $H_2S$ content) is passed through the central bore 62 of the inner flame tip member 60, while hydrogen gas is passed through the conduit (or conduits) 64 into the annular passageway 65. The combustion-supporting gas mixture from the central bore 62 thereupon mixes with the combustible gas exiting from the annular passageway 65 to form a hydrogen-rich gas mixture in the region immediately above the top end of the inner flame tip member 60. In operation, a first flame 70 is ignited at the top of the flame tip member 60 by a flashback process that is initiated by a conventional flame ignition means (e.g., the energizing of an electrically heated coil) applied to the top of the outer flame tip member 61.

Combustion products and unburned gases from this first flame 70 flow upward through the tubular flame tip member 61, and exit therefrom at a distance well removed from the top of the flame tip member 60. The combustion products and excess hydrogen from the first flame 70 rise through the flame tip member 61 to a region where additional oxygen or air is provided and a second flame 71 is ignited. Typically, the outside diameter of the flame tip member 61 is 0.44 inch at its largest dimension. For improved gas mixing characteristics, the upper portion of the flame tip member 61 is conically shaped to a reduced outside diameter of 0.18 inch at its smallest dimension. For flame tip members having the dimensions stated above, the top of the flame tip member 61 preferably extends 0.69 inch above the top of the flame tip member 60. The relatively thick wall of the outer flame tip member 61, which is made of a material (stainless steel) having a high thermal conductivity, provides a path of high thermal conductivity to a heat sink. The flame tip member 61 is disposed in thermally conductive relationship with other metallic components of the burner, whereby heat generated by the flames 70 and 71 can be dissipated. Hence, the thermal excitation of products outgassed from the flame tip members 60 and 61 is minimized.

In the preferred embodiment shown in FIG. 2, the outer flame tip member 61 is surrounded by a cylindrical tower 73, which provides a path for an oxygen-containing gas such as purified air to flow from conduit 66 along the outside length of the outer flame tip member 61 before mixing with the gases exiting from the flame tip member 61 in the region immediately above the upper end thereof. This relatively long flow path allows the air to establish a stable flow direction before mixing with the gases exiting from the flame tip member 61, which produces a stabilizing influence on the upper flame 71. For flame tip members having the dimensions stated above, an appropriate inside diameter for the tower 73 is 0.5 inch. In the embodiment shown in FIG. 2, the tower 73 is a component having a high thermal capacity for dissipating heat generated by the flames 70 and 71.

In operation, the upper flame 71 is ignited first. Flash back from the upper flame 71 then causes ignition of the lower flame 70. If the lower flame 70 is ever extinguished during operation due to solvent peaks, flash back from the upper flame 71 causes the lower flame 70 to be automatically reignited.

The upper flame 71 has a center core comprising hydrogen and combustion products from the lower flame 70, and an outer sheath of $O_2$ or air. The relative magnitudes of the flow rates of $O_2$ or air through the conduits 62 and 66, and of $H_2$ through the conduit 64, determine whether the flame 71 is predominantly a hydrogen-rich or an oxygen rich flame emission source. Selective flame photometric detection of only sulfur-bearing or phosphorus-bearing compounds requires a hydrogen-rich flame environment. For the flame-tip and tower dimensions stated above, flame 71 can be made hydrogen-rich by maintaining the following flow rates:

Air through conduit 62 at 80 milliliters per minute,
Air through conduit 66 at 170 milliliters per minute,
Hydrogen through conduit 64 at 140 milliliters per minute. For these gas flows through a burner having the dimensions stated above, the total quantity of oxygen supplied through the conduits 62 and 66 is sufficient to consume approximately 70% of the total quantity of hydrogen supplied. In comparison with the single-flame burner of the prior art discussed above in connection with U.S. Pat. No. 3,489,498, the dimensions and flow rates suggested herein for the preferred embodiment of the present invention represent a significant decrease in the quantity of unburned hydrogen expelled in the exhaust gases. The dimensions and flow rates suggested herein are not to be considered restrictive in practicing this invention. All dimensions can be either increased or decreased as long as the resulting gas flow rates result in stable flames 70 and 71, where the upper flame 71 is hydrogen-rich.

With hydrogen-rich gas flows as described above, sulfur-bearing and phosphorus-bearing compounds emit their characteristic blue and green colorations in a well-defined core region of the flame 71. These colorations occur in the core region, because this is the region of the flame that is most deficient in oxygen. In the outer periphery of the flame, where oxygen is more abundant, sulfur-indicative and phosphorus-indicative emissions diminish in intensity. Both the sulfur-indicative and the phosphorus-indicative emissions occur in the same spatial region of the flame 71, which thereby allows the same optical viewing axis to be used for either mode of selective detection. Furthermore, the spatial region of the upper flame 71 utilized for sulfur and/or phosphorus detection is relatively insensitive to variations in the flow rate of the carrier gas bringing the sample material into the lower flame 70, at least in range of from 10 to 100 milliliters per minute, through the conduit 62 for the flame-tip and tower dimensions stated above.

Unlike the upper flame of dual-flame burners known to the prior art, the core region of the upper flame 71 of a burner according to the present invention is not masked by an outer sheath of coloration caused by emissions from materials outgassed from the hot flame tips.

Figure 3:
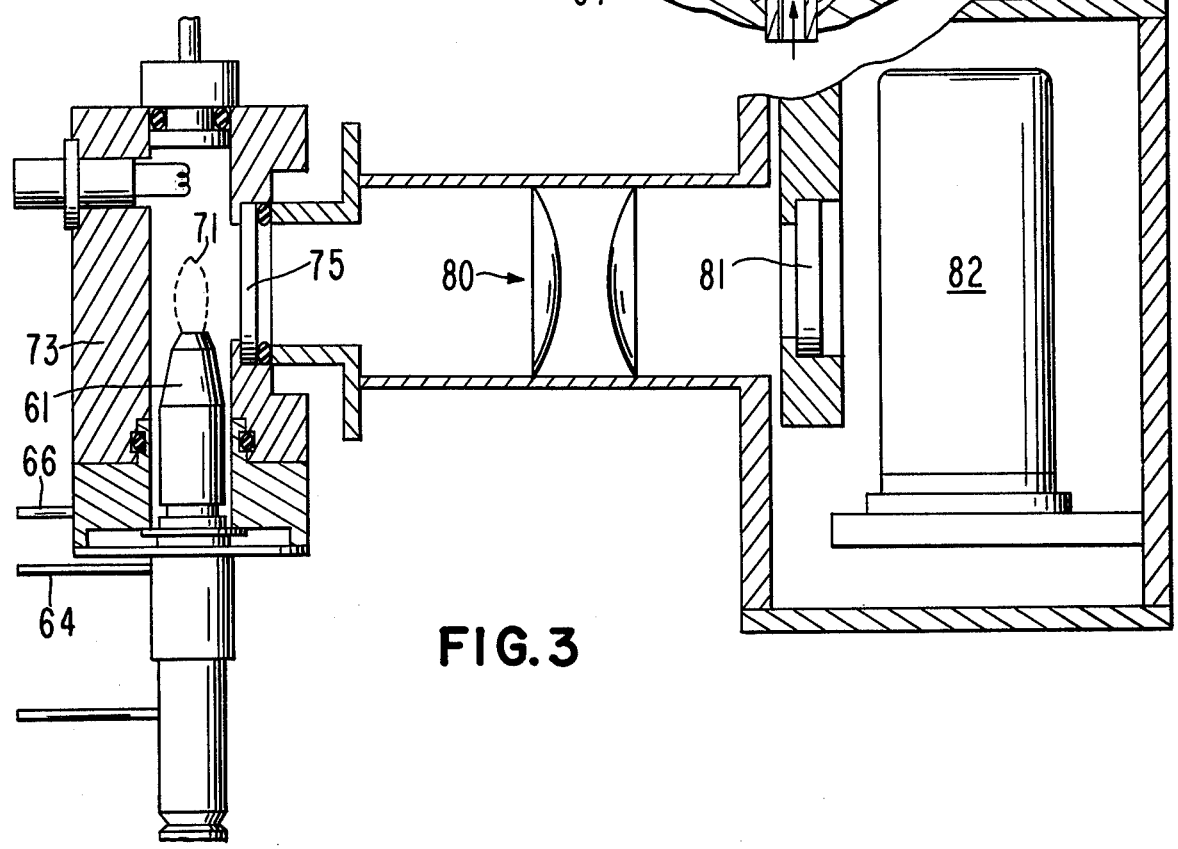
FIG. 3 is a schematic view of the burner of FIG. 2 in combination with spectrophotometric means for viewing the upper flame.

Detection of the emissions characteristic of the compounds of interest may be accomplished by conventional spectrophotometric techniques. An appropriate spectrophotometric technique is illustrated in FIG. 3, where emissions from the flame 71 are passed through an optical window 75 in the tower 73, into a suitable lens system 80, for transmission to a spectrally selective optical filter 81. The light frequency passing through the filter 81 falls incident upon a photomultiplier tube 82, which is connected to appropriate electronic circuitry for indicating (and, if desired, for providing a quantitative measurement of the intensity of) the presence of compounds of interest in the sample material. It is recognized that in certain applications, it might be advantageous to replace the filter 81 with a monochromator device.

In certain applications, for example, in the selective detection of nitrogen-bearing compounds, it is required that the upper flame 71 be oxygen-rich. For a burner having the flame-tip and tower dimensions stated above, the flame 71 can be made oxygen-rich by maintaining the following flow rates:

Air through conduit 62 at 80 millimeters per minute,
Air through conduit 66 at 300 milliliters per minute,
Hydrogen through conduit 64 at 70 milliliters per minute. For these gas flows through a burner having the dimensions stated above, the total quantity of oxygen supplied through the conduits 62 and 66 is more than sufficient to consume all of the hydrogen supplied. Again, the dimensions and flow rates suggested herein for maintaining an oxidizing flame are not to be considered as restrictive. All dimensions can be increased or decreased as long as the resulting gas flow rates result in stable flames 70 and 71, where the upper flame 71 is oxygen-rich.

The chemiluminescent reaction $NO + O \rightarrow NO_2 + h\nu$ has been observed in the past in flames where NO is a combustion product, e.g., in very hot hydrogen/air flames where $N_2$ from the air is decomposed.

This reaction has not heretofore been useful for analytical purposes in detecting the presence and quantity of nitrogen-containing compounds, because of the interfering radiations from other reactions. With a dual-flame burner according to the present invention, a quantitative measurement of nitrogen-containing compounds in a sample can be provided by viewing this chemiluminescent reaction in the upper flame 71, where interfering emissions from other reactions are suppressed.

In the technique of this invention, the nitrogen-containing compounds of the sample material are first combusted in the oxygen-containing lower flame 70 to produce, among other combustion products, nitric oxide. The NO then reacts with O atoms in the upper flame 71 to produce the chemiluminscent formation of $NO_2$.

The thorough mixing of the NO molecules in the region between the two flames results in a diffusion of NO molecules throughout the volume of the oxygen-rich upper flame 71, thereby enhancing the observability of the region of the flame in which the reaction occurs.

The radiation characteristic of the chemiluminescent $NO + O$ reaction can be observed by a spectrophotometric technique such as that discussed above in connection with FIG. 3. For optimum detection, a red-enhanced photomultiplier tube 82 should be used, along with a filter 81 that transmits light at selected wavelengths greater than 500 nanometers.

The present invention has been set forth in terms of specific embodiments. Nevertheless, variations in the flame viewing technique, as well as variations in the structural design of the burner itself, reside within the scope of the invention. For example, in certain applications it may be advantageous to view the upper flame from the top rather than from the side. Accordingly, the scope of the invention is limited only by the following claims.

What is claimed is:

1. A method for analyzing a chemical substance, said method comprising the steps of:
   introducing said chemical substance into a hydrogen-rich first flame,
   passing combustion products and excess hydrogen from said first flame into a second flame via a conduit structure having a substantial thermal conductance such that said conduit structure, in operation, does not contribute to the coloration of said second flame, and
   detecting the presence in said second flame of a color that is indicative of the presence of a particular constituent in said chemical substance.

2. The method of claim 1 wherein the color indicative of the presence of a particular constituent in said chemical substance is detected by spectrophotometric means.

3. The method of claim 2 wherein said spectrophotometer means comprises means for observing said second flame by a photomultiplier through an optical filter.

4. The method of claim 1 wherein the oxygen content in a peripheral region of said second flame is controllable.

5. The method of claim 4 wherein the oxygen content in said peripheral region of said second flame is decreased for depriving said second flame of sufficient oxygen to react with all of the hydrogen in the second flame, thereby providing a hydrogen-rich second flame.

6. The method of claim 5 wherein said detecting step comprises detecting a blue color in said second flame indicative of sulfur.

7. The method of claim 5 wherein said detecting step comprises detecting a green color in said second flame indicative of phosphorus.

8. The method of claim 4 wherein the oxygen content in said peripheral region of said second flame is increased to provide more than sufficient oxygen to react with all of the hydrogen in said second flame, thereby providing an oxygen-rich second flame.

9. The method of claim 8 wherein said detecting step comprises detecting a coloration of said second flame resulting from a chemical reaction indicative of elemental carbon.

10. The method of claim 8 wherein said detecting step comprises detecting a coloration of said second flame resulting from a chemical reaction indicative of elemental nitrogen.

11. The method of claim 10 wherein said chemical reaction comprises a chemiluminescent molecular recombination of nitric oxide and oxygen atoms to form nitrogen dioxide molecules.

12. A two-flame burner for use in analyzing a sample material, said burner comprising:
   an inner conduit structure, an end of which defines a first flame tip;
   an outer conduit structure, an end of which defines a second flame tip;

said first and second flame tips being spatially separated;

said inner conduit structure being disposed within said outer conduit structure to provide a passageway between said conduit structures for hydrogen, an oxydizing gas and said sample material to a region adjacent said first flame tip, thereby permitting a hydrogen-rich first flame to be maintained adjacent said first flame tip;

said outer conduit being configured to cause combustion products and excess hydrogen from said first flame to exit at said second flame tip, thereby permitting a second flame to be maintained in an oxygen-containing environment adjacent said second flame tip;

said inner and outer conduit structures being chemically inert with respect to combustion products of said first flame;

said inner and outer conduit structures being disposed in thermally conductive relationship with a heat sink, whereby said conduit structures do not contribute to coloration of said second flame during operation of said burner.

13. The burner of claim 12 wherein said inner conduit structure is composed of a stainless steel.

14. The burner of claim 12 wherein said inner conduit structure is composed of a ceramic material.

15. The burner of claim 12 wherein said outer conduit structure is composed of a stainless steel.

16. The burner of claim 12 wherein said outer conduit structure is composed of a ceramic material.

17. The burner of claim 12 wherein a means is provided for introducing an oxygen-containing gas at a controlled flow rate into the region adjacent said second flame tip.

18. The burner of claim 17 wherein said means for introducing said oxygen-containing gas into the region adjacent said second flame tip comprises a tower structure enclosing said inner and outer conduit structures.

19. The burner of claim 18 in combination with spectrophotometric means for detecting a particular constituent in said sample material.

20. The burner of claim 12 in combination with spectrophotometric means for detecting a particular constituent in said sample material.

21. The combination of claim 20 wherein said spectrophotometric means comprises means for observing a chemiluminescent molecular recombination of nitric oxide and oxygen atoms to form nitrogen dioxide molecules.

22. The combination of claim 20 wherein said spectrophotometric means comprises photomultiplier means.

23. The combination of claim 22 wherein said photomultiplier means is used in conjunction with an optical filter.

24. The burner of claim 12 wherein said inner and outer conduit structures are of generally cylindrical configuration and are coaxially disposed with respect to each other.

25. The burner of claim 24 wherein access for hydrogen to the region adjacent said first flame tip is provided via the passageway between said inner conduit structure and said outer conduit structure.

26. The burner of claim 25 in combination with spectrophotometric means for detecting a particular constituent in said sample material.

27. The burner of claim 24 wherein access for the oxidizing gas and said sample material to the region adjacent said first flame tip is provided via said inner conduit structure.

28. The burner of claim 27 in combination with spectrophotometric means for detecting a particular constituent in said sample material.

29. A method for detecting nitrogen-bearing compounds in a sample material by reacting said sample material to produce nitric oxide molecules, and by observing a chemiluminescent reaction of said nitric oxide molecules with oxygen atoms to form nitrogen dioxide molecules, said method comprising the steps of:
   introducing said sample material into a first flame to produce combustion products that include nitric oxide,
   passing and nitric oxide into an oxidizing second flame, and
   observing a coloration in said second flame indicative of said chemiluminescent reaction.

* * * * *